(12) United States Patent
Zhang et al.

(10) Patent No.: US 11,614,717 B2
(45) Date of Patent: Mar. 28, 2023

(54) WEARABLE DETECTION DEVICE

(71) Applicant: GOERTEK TECHNOLOGY CO., LTD., Qingdao (CN)

(72) Inventors: Zhongli Zhang, Qingdao (CN); Weixian Zou, Qingdao (CN); Jinwei Wang, Qingdao (CN)

(73) Assignee: GOERTEK TECHNOLOGY CO., LTD., Qingdao (CN)

( * ) Notice: Subject to any disclaimer, the term of this patent is extended or adjusted under 35 U.S.C. 154(b) by 388 days.

(21) Appl. No.: 16/606,183

(22) PCT Filed: Oct. 27, 2017

(86) PCT No.: PCT/CN2017/108010
§ 371 (c)(1),
(2) Date: Oct. 17, 2019

(87) PCT Pub. No.: WO2018/214399
PCT Pub. Date: Nov. 29, 2018

(65) Prior Publication Data
US 2020/0125038 A1    Apr. 23, 2020

(30) Foreign Application Priority Data
May 24, 2017 (CN) .......................... 201710375438.1

(51) Int. Cl.
*G04G 21/02* (2010.01)
*A44C 5/00* (2006.01)
(Continued)

(52) U.S. Cl.
CPC ......... *G04G 21/025* (2013.01); *A44C 5/0053* (2013.01); *A61B 5/02438* (2013.01); *A61B 5/681* (2013.01)

(58) Field of Classification Search
CPC .... G04G 21/025; G04G 17/06; A44C 5/0053; A44C 5/0023; A44C 5/2071;
(Continued)

(56) References Cited

U.S. PATENT DOCUMENTS

2006/0253010 A1    11/2006  Brady et al.
2016/0022210 A1*    1/2016  Nuovo ................... A61B 5/318
                                                    600/301
(Continued)

FOREIGN PATENT DOCUMENTS

CN         103393414 A       11/2013
CN         104000571 A        8/2014
(Continued)

OTHER PUBLICATIONS

Office Action dated May 5, 2019 for Chinese patent application No. 201710375438.1.

*Primary Examiner* — Eric F Winakur
*Assistant Examiner* — Abid A Mustansir
(74) *Attorney, Agent, or Firm* — Maschoff Brennan

(57) ABSTRACT

A wearable detection device includes a main body, a first belt body, and a second belt body. The first belt body and the second belt body are connected to two sides of the main body. The main body includes a power source, a control circuit connected to the power source, and a processor connected to the control circuit. The wearable detection device further includes a flexible circuit board and a plurality of to-be-conducted chips. The flexible circuit board is disposed in the first belt body and is connected to the main body. The plurality of to-be-conducted chips are disposed in the first belt body and are connected to the flexible circuit board. When the first belt body and the second belt body are interconnected, the to-be-conducted chip positioned at a junction point is connected.

9 Claims, 3 Drawing Sheets

(51) Int. Cl.
*A61B 5/024* (2006.01)
*A61B 5/00* (2006.01)

(58) Field of Classification Search
CPC ....... A61B 5/02438; A61B 5/681; A61B 5/01;
A61B 5/02141; A61B 2560/0425; A61B
2562/166; A61B 5/02; A61B 5/0205;
A61B 5/021; A61B 5/024; A61B 5/6824
See application file for complete search history.

(56) References Cited

U.S. PATENT DOCUMENTS

| | | | |
|---|---|---|---|
| 2016/0070393 A1* | 3/2016 | Sharma | A61B 5/002 |
| | | | 345/174 |
| 2016/0089053 A1* | 3/2016 | Lee | A61B 5/0537 |
| | | | 600/384 |
| 2016/0209875 A1* | 7/2016 | Kim | G06F 1/1652 |
| 2017/0007183 A1* | 1/2017 | Dusan | A61B 5/02416 |
| 2017/0347895 A1* | 12/2017 | Wei | A61B 5/01 |

FOREIGN PATENT DOCUMENTS

| | | |
|---|---|---|
| CN | 104188636 A | 12/2014 |
| CN | 105796073 A | 7/2016 |
| CN | 107041738 A | 8/2017 |
| CN | 207654149 U | 7/2018 |

\* cited by examiner

WEARABLE DETECTION DEVICE

CROSS-REFERENCE TO RELATED APPLICATIONS

This application claims priority to Chinese Patent Application No. 201710375438.1, entitled "Wearable Detection Device", filed on May 24, 2017, which is hereby incorporated by reference in its entirety.

FIELD

The present application belongs to the field of smart wear, and in particular, to a wearable detection device.

BACKGROUND

At the present stage, smart wearable devices are developing rapidly and have been accepted by more and more users. For example, a sports smart wristband or watch is mainly used for real-time detection of human health parameters and motion parameters.

However, the detection chip of the health electronic product such as the wristband or the watch at the present stage is located in the part of the device body. The detection chip is located on the back of the wrist when worn by the user on the wrist, and generally protrudes from the device body in order to fully contact the human body. It is well known that the best position for detecting human health parameters is located at the arterial position of the wrist, which is that the human health parameters detected by the position of the back of the wrist are not accurate enough, and the design of the detection chip protruding from the body of the device greatly reduces the wearing comfort. In addition, the existing detection chip does not detect the pulse, which makes the detected human health parameters incomplete.

In short, the existing smart wearable device has technical problems of inaccurate and incomplete detected data, and poor wearing comfort.

SUMMARY

In view of this, the embodiment of the present application provides a wearable detection device for solving the technical problems of the existing smart wearable device of inaccurate and incomplete detected data, and poor wearing comfort.

An embodiment of the present application provides a wearable detection device, including a main body, a first belt body and a second belt body, where the first belt body and the second belt body are connected to two sides of the main body respectively, the main body includes a power source, a control circuit connected to the power source, a processor connected to the control circuit, a flexible circuit board and a plurality of to-be-conducted chips;

the flexible circuit board is disposed in the first belt body and is connected to the main body, and the plurality of to-be-conducted chips are disposed in the first belt body and are connected to the flexible circuit board;

and where when the first belt body and the second belt body are interconnected, the to-be-conducted chip positioned at a junction point is conducted.

Further, the first belt body is provided with a plurality of buckle holes, and the plurality of to-be-conducted chips are respectively disposed at a periphery of the plurality of buckle holes.

Further, the second belt body is provided with a pin, the pin is used for buckling into any one of the plurality of buckle holes, and when the pin is buckled into any one of the plurality buckle holes, the to-be-conducted chip at the periphery of the buckle hole is conducted.

Further, the plurality of to-be-conducted chips are respectively a ring-shaped chip having a notch, and a chip spring is disposed at the notch, and when the pin is buckled into any one of the plurality buckle holes, the chip spring is squeezed to make the slip disappear, and the to-be-conducted chip is conducted.

Further, an inner diameter of the plurality of buckle holes is smaller than an outer diameter of a periphery of the pin.

Further, one end of the pin away from the second belt body is a fixing cover, and a diameter of the fixing cover is larger than an outer diameter of the periphery of the pin.

Further, the first belt body and the second belt body are made of a flexible material.

Further, the flexible material comprises: fluororubber or silica gel.

Further, the to-be-conducted chip is conducted for detecting a human health parameter.

Further, the human health parameter comprises at least one of a pulse, a heart rate, a blood pressure, and a body temperature.

According to the wearable detection device provided by the embodiment of the present application, when the first belt body and the second belt body respectively connected to the main body are connected to each other, the to-be-conducted chip positioned at a junction point is conducted, and the human health parameter is detected. By the change of the position of the detection chip of the wearable detection device, the accuracy and the completeness of the detected human health data are improved, and the wearing comfort of the user is increased.

BRIEF DESCRIPTION OF THE DRAWINGS

In order to describe the technical solutions in the embodiments of the present invention or the prior art more clearly, the drawings required to be used for descriptions about the embodiments or the prior art will be simply introduced below. It is apparent that the drawings described below are some embodiments of the present invention. Those of ordinary skill in the art may further obtain other drawings according to these drawings without creative work.

DETAILED DESCRIPTION OF EXAMPLE EMBODIMENTS

For the purpose of making objectives, technical schemes and advantages of the present application more clear, clear and complete description will be made to the technical schemes of the present application in conjunction with specific embodiments and corresponding drawings. Obviously, the described embodiments are merely a part of the embodiments of the present application and not all the embodiments. Based on the embodiments of the present application, all other embodiments obtained by those ordinarily skilled in the art without paying creative work fall within the protection scope of the present application.

Figure 1:
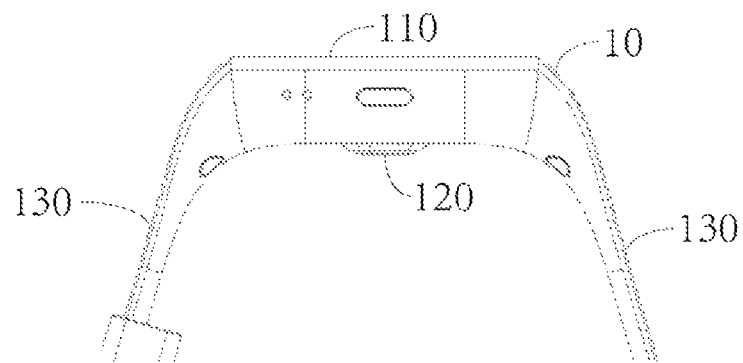
FIG. 1 is a schematic cross-sectional view of a prior art smart watch.
Figure 2:
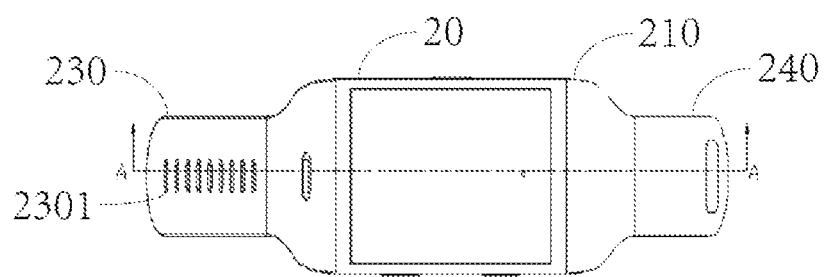
FIG. 2 is a schematic plan view of a wearable detection device according to an embodiment of the present application.
Figure 3:
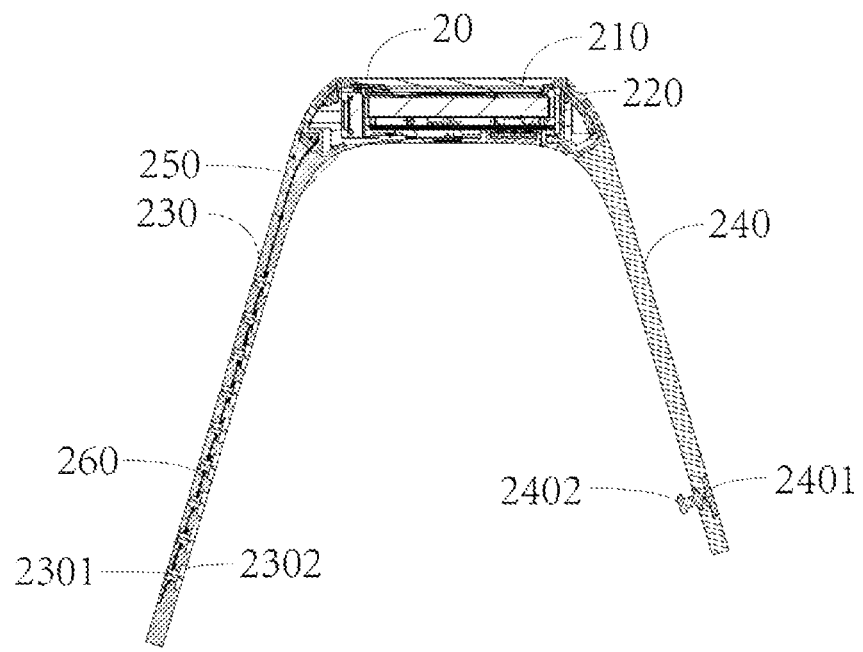
FIG. 3 is a cross-sectional view taken along the line A-A of FIG. 2 of the wearable detection device according to an embodiment of the present application.
Figure 4:
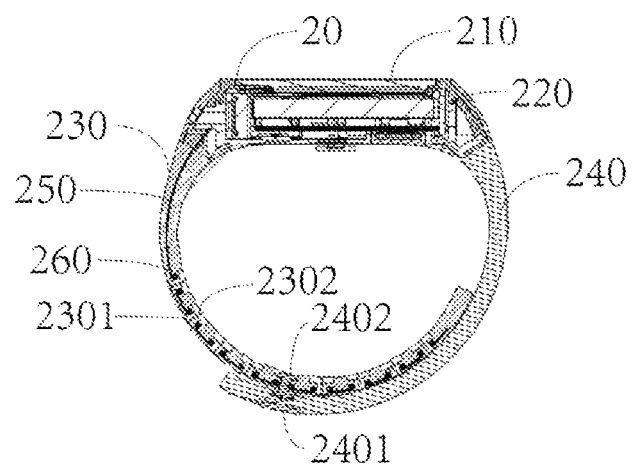
FIG. 4 is a cross-sectional view showing a connection state of a wearable detection device according to an embodiment of the present application.
Figure 5:
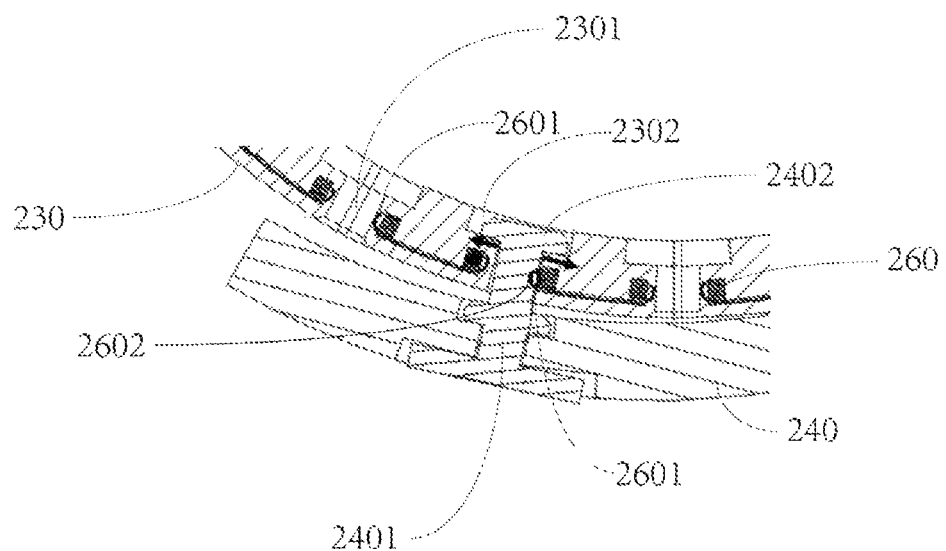
FIG. 5 is an enlarged cross-sectional view showing a connection point of a wearable detection device according to an embodiment of the present application.
Figure 6:
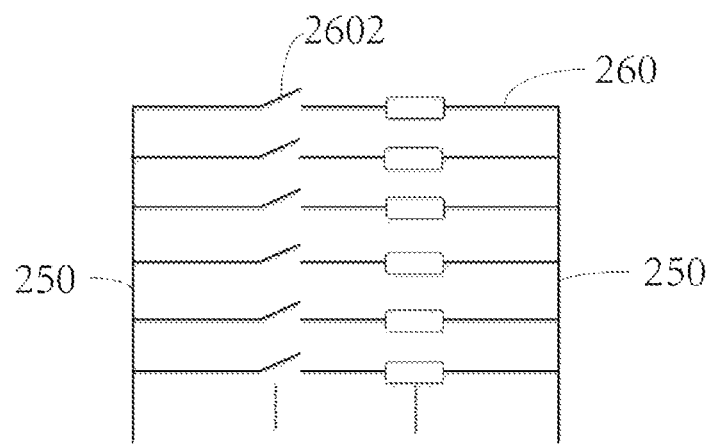
FIG. 6 is a circuit diagram of a detection chip of a wearable detection device according to an embodiment of the present application.

Please refer to the following figures, FIG. 1 is a schematic cross-sectional view of a prior art smart watch; FIG. 2 is a schematic plan view of a wearable detection device according to an embodiment of the present application; FIG. 3 is a cross-sectional view taken along the line A-A of FIG. 2 of the wearable detection device according to an embodiment of the present application; FIG. 4 is a cross-sectional view showing a connection state of a wearable detection device according to an embodiment of the present application; FIG. 5 is an enlarged cross-sectional view showing a connection point of a wearable detection device according to an embodiment of the present application; and FIG. 6 is a circuit diagram of a detection chip of a wearable detection device according to an embodiment of the present application.

In the existing wearable detection device, such as the smart watch 10 shown by FIG. 1, a detection chip 120 is provided on a back of a watch head 110 connected to the left and right watch bands 130, and the detection chip 120 is used for detecting a human health parameter. But the health parameter herein does not include the pulse parameter, resulting in incomplete detected data. Even if the pulse parameter is included, it is well known that the best position for detecting the pulse is located on the inside of the wrist rather than on the back side of the wrist, which results in inaccurate detected data. Moreover, multiple arteries connected to the human heart are gathered inside the wrist, and human health data detected inside the wrist is more accurate and those detected through the back of the wrist is inaccurate vice versa. In addition, as shown in FIG. 1, in order to allow the detection chip 120 and the back of the wrist are fully contacted, the detection chip 120 is generally designed to be projected. In this case, it is easy to hit the wrist and even damage the skin, so that the wearing experience is poor, that is, the smart watch 10 in the prior art of FIG. 1 has technical problems of inaccurate and incomplete detected data, and poor wearing comfort.

Please refer to FIGS. 2-6, in order to solve the above technical problems, the embodiment of the present application provides a wearable detection device, which is not limited to a smart watch. The present embodiment is described by taking the smart watch as an example, but does not constitute a limitation on the present application.

The smart watch 20 of the present application includes a watch head 210, a main body 220 disposed inside the watch head 210, a first belt body 230, a second belt body 240, a flexible circuit board 250, and a plurality of to-be-conducted chips 260.

The first belt body 230 and the second belt body 240 are respectively disposed on both sides of the watch head 210 and are detachably connected to the watch head 210.

The main body 220 further includes a power source, a control circuit connected to the power source, a processor connected to the control circuit, and a display screen. The above components are not shown in the figures, and are not different from the ordinary smart watch or the sports watch.

The flexible circuit board 250 is disposed in the first belt body 230 and is connected to the main body 220. The plurality of to-be-conducted chips 260 are also disposed in the first belt body 230, and each of the plurality of to-be-conducted chips 260 is respectively connected to the flexible circuit board 250. When the first belt body 230 and the second belt body 240 are connected to each other, the to-be-conducted chip 260 at the connection point is conducted.

Specifically, the first belt body 230 is provided with a plurality of buckle holes 2301, and the plurality of to-be-conducted chips 260 are respectively disposed at the periphery of the plurality of buckle holes 2301, that is, the number of the buckle holes 2301 is same to the number of the to-be-conducted chips 260, and the number thereof is related to the actual lengths of the first strip 230 and the second strip 240. Generally, the longer the lengths of the first strip 230 and the second strip body 240 are, the more the number is. The buckle holes 2301 can be, but is not limited to, a circular through hole, and the to-be-conducted chip 260 is a ring-shaped chip, which is concentric with the buckle hole 2301. The second belt body 240 is provided with a pin 2401, and the pin 2401 is used for buckling into any one of the plurality of the buckle holes 2301. When the pin 2401 is buckled into any one of the buckle holes 2301, the to-be-conducted chip at the periphery of the buckle hole 2301 is conducted.

Herein, the plurality of to-be-conducted chips 260 are respectively a ring-shaped chip having a notch 2601, and a chip spring 2602 is disposed at the notch 2601. When the pin 2401 is buckled into any one of the plurality of the buckle holes 2301, the chip spring 2602 is squeezed to make the notch 2601 disappear, and the to-be-conducted chip 260 is conducted.

The conduction mechanism of the plurality of to-be-conducted chips 260 is as follows: when the pin 2401 is not buckled into the buckle hole 2301, the chip spring 2602 is not squeezed, the to-be-conducted chip 260 has a notch, and the to-be-conducted chip 260 is not conducted; when the pin 2401 is buckled into the buckle hole 2301, the chip spring 2602 is squeezed, the notch 2601 of the to-be-conducted chip 260 disappears, and the to-be-conducted chip 260 is in a state of being conducted.

When the to-be-conducted chip 260 is in the state of being conducted, it is used to detect a human health parameter, and the first belt body 230 and the second belt body 240 are connected to each other. The connection point position is located at the opposite side of the watch head 210, that is, located on the inner side of the wrist of the human body. At this time, the detection of the human health parameter is relatively accurate.

The human health parameter herein includes at least one of a pulse, a heart rate, a blood pressure, and a body temperature, that is, may detect one of the pulse, the heart rate, the blood pressure and the body temperature, or may detect more than one of the pulse, the heart rate, the blood pressure, and the body temperature. The specific detection items are related to the type of the to-be-conducted chip 260. Different types of the to-be-conducted chips 260 detect different human health parameters. By the setting the to-be-conducted chips 260 detecting multiple human health parameter, the completeness of the detected human health parameters of the smart watch 20 is ensured.

It should be noted that the inner diameter of the plurality of the buckle holes 2301 is smaller than an outer diameter of a periphery of the pin 2401, that is, on one hand, when the pin 2401 is buckled into the buckle hole 2301, the chip spring 2602 may be pressed to make the notch 2601 disappear, thereby causing the to-be-conducted chip 260 to be conducted; on the other hand, the connection between the first belt body 230 and the second belt body 240 may be made more reliable and enhance the user's wearing experience.

In addition, the to-be-conducted chip 260 is conducted only when the first belt body 230 and the second belt body 240 are connected to each other, that is, when being worn, and the human body data detection function of the smart watch 10 is activated at this time, which avoids the waste of power when the detection chip is still in working state when it is not worn, and improves the service life of the smart watch.

In a preferred embodiment, one end of the pin 2401 away from the second belt body 240 is a fixed cover 2402. The diameter of the fixing cover 2402 is larger than the outer diameter of the periphery of the pin 2401. Specifically, a free end of the pin 2401 sets the fixing cover 2402. When the first belt body 230 and the second belt body 240 are connected to each other, that is, when the pin 2401 is buckled into the buckle hole 2301, the fixing cover 2402 protrudes from the buckle hole 2301, and the diameter of the fixing cover 2402 is larger than the diameter of the buckle hole 2301, so that the connection between the first belt 230 and the second belt 240 is more fasten.

Further, a groove 2302 is provided around the buckle hole 2301 inside the first belt body 230, the fixing cover 2402 falls into the groove 2302, and an end surface of the fixing cover 2402 is flush to the inner side of the first belt body 230. This design ensures that the position where the detection chip and the human skin contact each other does not have a convexity, and does not reach the wrist, thereby enhancing the wearing experience of the user.

In addition, the first belt body 230 and the second belt body 240 are made of a flexible material, and the flexible material herein refers to a soft material that may be used to make a watch band, which may be, but not limited to, a fluororubber or silica gel. The watch band made of this flexible material may guarantee the flexibility of use, and also ensure the wearing comfort of the user to further enhance the user's wearing experience.

The smart watch provided by the embodiment of the present application is only an example of the wearable detection device to be protected by the present application. It is conceivable that the smart watch may be worn on other parts of the human body (such as the leg, the waist, the back, etc.). When the first belt body and the second belt body respectively connected to the main body are connected to each other, the to-be-conducted chip at the connection point is conducted and detects the human health parameter. By the change of the position of the detection chip of the wearable detection device, the accuracy and the completeness of the detected human health data are improved, and the wearing comfort of the user is increased.

Through the description of the above embodiments, those skilled in the art can clearly understand that the various embodiments can be implemented by means of software with a necessary general hardware platform, and of course, by hardware. Based on such understanding, the above-described technical solutions in essence or the part that makes contributes to the prior art may be embodied in the form of software products, which may be stored in a computer readable storage medium such as ROM/RAM, magnetic discs, optical discs, etc., including instructions for causing a computer device (which may be a personal computer, server, or network device, etc.) to perform the methods described in various embodiments or portions of the embodiments.

It is finally to be noted that the above embodiments are adopted not to limit but only to describe the technical solutions of the present disclosure. Although the present disclosure has been described with reference to the above-mentioned embodiments in detail, those of ordinary skill in the art should know that modifications may still be made to the technical solutions recorded in each embodiment or equivalent replacements may be made to part of technical features therein. These modifications or replacements do not make the essences of the corresponding technical solutions depart from the spirit and scope of the technical solutions of each embodiment of the present disclosure.

What is claimed is:

1. A wearable detection device, comprising a main body, a first belt body, a second belt body, a flexible circuit board and a plurality of unelectrified chips;
   wherein, the first belt body and the second belt body are connected to two sides of the main body respectively, and the main body comprises a power source, a control circuit connected to the power source, and a processor connected to the control circuit;
   the flexible circuit board is disposed in the first belt body and is connected to the main body, and the plurality of unelectrified chips are disposed in the first belt body and are connected to the flexible circuit board;
   wherein when the first belt body and the second belt body are interconnected, the unelectrified chips positioned at a junction point are supplied with electricity;
   wherein, the first belt body is provided with a plurality of buckle holes, and the plurality of unelectrified chips are respectively disposed at a periphery of the plurality of buckle holes; and
   wherein the second belt body is provided with a pin, the pin is used for buckling into any one of the plurality of buckle holes, and when the pin is buckled into any one of the plurality of the buckle holes, the unelectrified chips at the periphery of the buckle hole is supplied with electricity.

2. The wearable detection device according to claim 1, wherein the plurality of unelectrified chips are respectively a ring-shaped unelectrified chip having a notch, and a spring is disposed at the notch, and when the pin is buckled into any one of the plurality of the buckle holes, the spring is squeezed to make the notch disappear, and the unelectrified chip is supplied with electricity.

3. The wearable detection device according to claim 1, wherein an inner diameter of the plurality of buckle holes is smaller than an outer diameter of a periphery of the pin.

4. The wearable detection device according to claim 3, wherein one end of the pin away from the second belt body is a fixing cover, and a diameter of the fixing cover is larger than an outer diameter of the periphery of the pin.

5. The wearable detection device according to claim 1, wherein the first belt body and the second belt body are made of a flexible material.

6. The wearable detection device according to claim 5, wherein the flexible material comprises: fluororubber or silica gel.

7. The wearable detection device according to claim 1, wherein the unelectrified chip is supplied with electricity for detecting a human health parameter.

8. The wearable detection device according to claim 7, wherein the human health parameter comprises at least one of a pulse, a heart rate, a blood pressure, and a body temperature.

9. The wearable detection device according to claim 2, wherein an inner diameter of the plurality of buckle holes is smaller than an outer diameter of a periphery of the pin.

* * * * *